United States Patent
Young et al.

(10) Patent No.: US 11,617,500 B2
(45) Date of Patent: Apr. 4, 2023

(54) DILATION DEVICES, METHODS, AND SYSTEMS

(71) Applicant: i360medical Ltd., Dublin (IE)

(72) Inventors: Derek Young, Dublin (IE); Raymond O'Sullivan, Kilkenny (IE); Walter Prendiville, Kilcock (IE); Richard Gribbons, Dublin (IE)

( * ) Notice: Subject to any disclaimer, the term of this patent is extended or adjusted under 35 U.S.C. 154(b) by 428 days.

(21) Appl. No.: 16/774,222

(22) Filed: Jan. 28, 2020

(65) Prior Publication Data

US 2020/0237206 A1 Jul. 30, 2020

Related U.S. Application Data

(60) Provisional application No. 62/797,863, filed on Jan. 28, 2019.

(51) Int. Cl.
*A61B 1/32* (2006.01)
*A61B 1/06* (2006.01)
*A61M 29/00* (2006.01)
*A61B 1/00* (2006.01)

(52) U.S. Cl.
CPC ........ *A61B 1/0684* (2013.01); *A61B 1/00042* (2022.02); *A61B 1/06* (2013.01); *A61B 1/32* (2013.01); *A61M 29/00* (2013.01)

(58) Field of Classification Search
CPC ... A61B 1/31–32; A61B 1/06; A61B 17/0218; A61M 29/00
USPC ................................ 600/220–224, 184–185
See application file for complete search history.

(56) References Cited

U.S. PATENT DOCUMENTS

| | | | | |
|---|---|---|---|---|
| 2,544,932 A * | 3/1951 | Marco | ....................... | A61B 1/32 600/222 |
| 2,809,628 A * | 10/1957 | Jonas | ....................... | A61B 1/32 600/222 |
| 3,841,317 A * | 10/1974 | Awais | ................. | A61B 1/00142 600/203 |
| 5,190,555 A * | 3/1993 | Wetter | ............. | A61B 17/00234 606/1 |
| 5,460,165 A * | 10/1995 | Mayes | ............... | A61B 1/00142 600/203 |
| 5,545,122 A * | 8/1996 | Spruill | ..................... | A61B 1/32 604/99.04 |
| 6,432,048 B1 * | 8/2002 | Francois | .................. | A61B 1/32 600/220 |
| 6,902,530 B1 * | 6/2005 | Pianka | ............... | A61B 1/00142 600/220 |
| 7,063,664 B2 * | 6/2006 | Mohajer | ................ | A61B 1/303 600/184 |
| 8,460,187 B2 * | 6/2013 | Bouquet | .................. | A61B 1/32 600/222 |
| 2004/0236186 A1 * | 11/2004 | Chu | ........................ | A61B 1/32 600/215 |
| 2007/0038216 A1 * | 2/2007 | Hamada | ................. | A61B 17/02 606/53 |
| 2008/0058605 A1 * | 3/2008 | Sorensen | ................ | A61B 1/32 600/208 |

(Continued)

*Primary Examiner* — Jessica Weiss
(74) *Attorney, Agent, or Firm* — Bookoff McAndrews, PLLC

(57) ABSTRACT

According to one aspect, a dilation device may include a body, at least one loop actuator attached to the body, and a sheath attached to the body at a proximal end and attached to the loop actuator at a distal end.

20 Claims, 4 Drawing Sheets

(56) References Cited

U.S. PATENT DOCUMENTS

| | | | |
|---|---|---|---|
| 2008/0228038 A1* | 9/2008 | McMahon | A61B 1/0684 600/223 |
| 2009/0097236 A1* | 4/2009 | Miller | A61B 90/30 362/119 |
| 2009/0149857 A1* | 6/2009 | Culbert | A61B 1/00071 606/191 |
| 2014/0163322 A1* | 6/2014 | Mehta | A61B 1/00135 600/203 |
| 2015/0272564 A1* | 10/2015 | Piskun | A61B 1/00066 600/114 |

* cited by examiner

DILATION DEVICES, METHODS, AND SYSTEMS

CROSS-REFERENCE TO RELATED APPLICATION(S)

This patent application claims the benefit under 35 U.S.C. § 119 to U.S. Provisional Patent Application No. 62/797,863, filed on Jan. 28, 2019, the entirety of which is incorporated herein by reference.

BACKGROUND

Numerous medical procedures require dilation of a body lumen, such as those specific to the female reproductive system. A metal speculum is commonly used to perform these procedures. Metal speculums often rely upon mechanical ratchets, or like mechanisms, to maintain the speculum in an expanded position. These mechanisms may not provide the surgeon with adequate control over the amount of dilation, thus causing discomfort or vaginal injury, such as tearing. Metallic speculums can also be cold, adding further discomfort. Further improvements are required.

BRIEF DESCRIPTION OF THE DRAWINGS

The accompanying drawings, which are incorporated in and constitute a part of this specification, illustrate exemplary aspects that, together with the written descriptions, serve to explain the principles of this disclosure.

DETAILED DESCRIPTION

The present disclosure is now described with reference to exemplary aspects of dilation devices, methods, and systems. Some aspects are depicted and/or described with reference to a particular body orifice or lumen, such as the vagina, rectum, mouth, or other naturally occurring orifices; while other aspects reference a particular procedure, such as those specific to any of these orifices or lumens. These references are provided for convenience and not intended to limit the present disclosure unless incorporated into the appended claims. Accordingly, the concepts and novelty underlying each aspect may be utilized for any analogous type of lumen or orifice, natural or otherwise; or procedure, medical or otherwise.

The directional terms "proximal" and "distal" are used to describe relative components and features of the present disclosure. The term proximal refers to a position closer to the exterior of the body or a user, whereas the term distal refers to a position closer to the interior of the body or further away from the user. Unless claimed, these directional terms are provided for convenience and not intended to limit the present disclosure to a particular direction or orientation.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. Unless stated otherwise, the term "exemplary" is used in the sense of "example," rather than "ideal."

Figure 1:
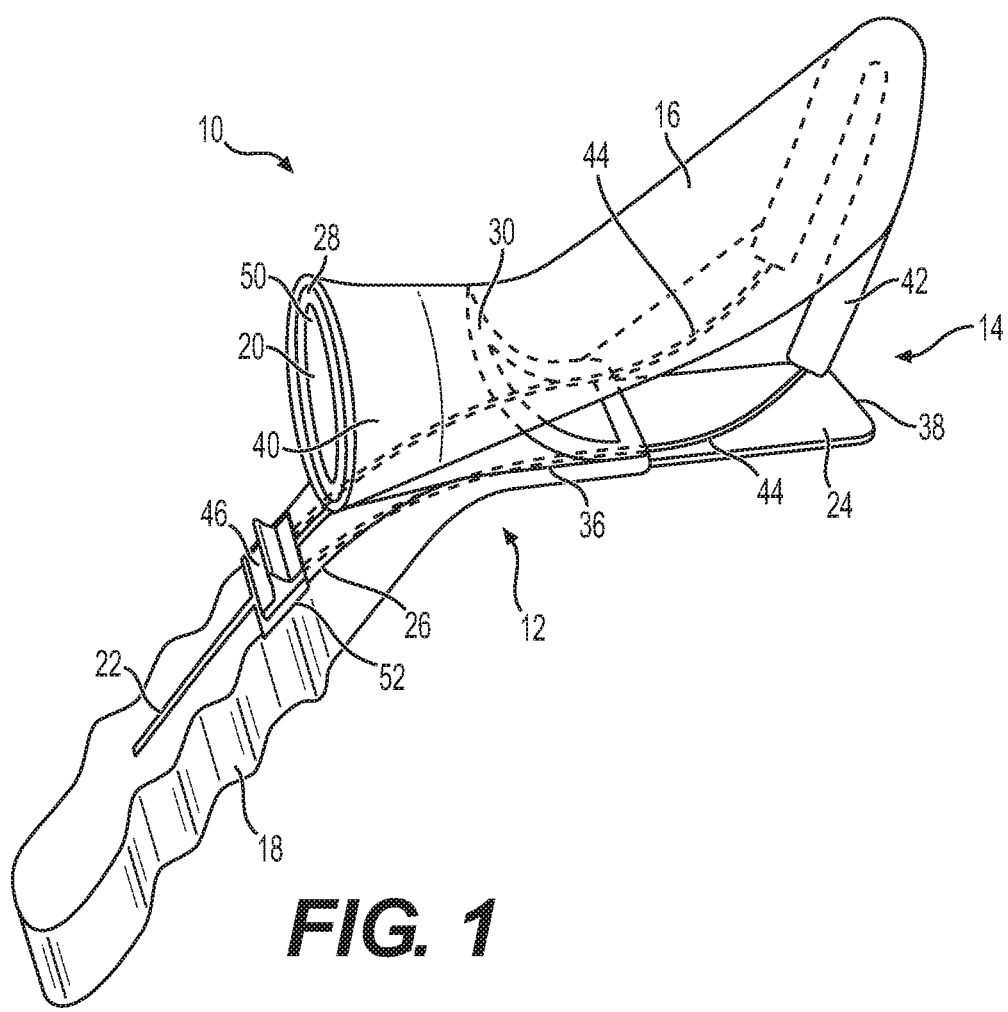
FIG. 1 depicts an exemplary dilation device in its open position.

One aspect of the present disclosure is depicted in FIG. 1 as a dilation device, such as a speculum 10. The speculum 10 of FIG. 1 comprises a body 12, a loop actuator 14 attached to the body 12, and a movable sheath 16 that is attached to the body 12 at a proximal end and to loop actuator 14 at a distal end.

The body 12 may include a handle 18, a tubular portion 20 located at a distal end of the handle 18, and a lower jaw 24 extending distal from the handle 18. The handle 18 extends proximally to provide a grip for the dilation device 10. The handle 18 may be angled relative to the lower jaw 24 to form an obtuse angle to facilitate a comfortable and/or ergonomic use of the dilation device 10 for patients or medical practitioners, or both. The handle 18 may include an actuator groove 22 extending centrally along a proximal side of the handle 18. The actuator groove 22 is configured to guide movement of the loop actuator 14 between the speculum open and closed positions. Further, the actuator groove 22 may include a locking recess 52 for securing the loop actuator 14 in the open configuration. The handle 18 may also include internal passageways 26 for distally extending portions of the loop actuator 14, as will be described in more detail below. The handle 18 may be in any shape, size, or design. For instance, the handle may be in the shape of cylinder, cone, cuboid, or triangular prism, and may include any conventional gripping grooves such as the grooves shown.

Figure 2:
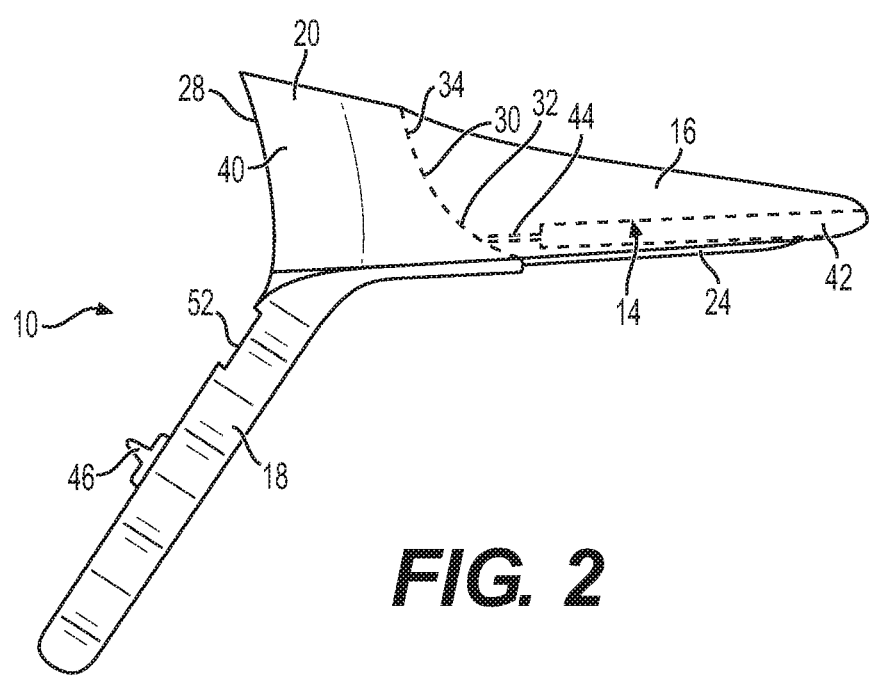
FIG. 2 depicts the exemplary dilation device of FIG. 1 in its closed position.
Figure 3:
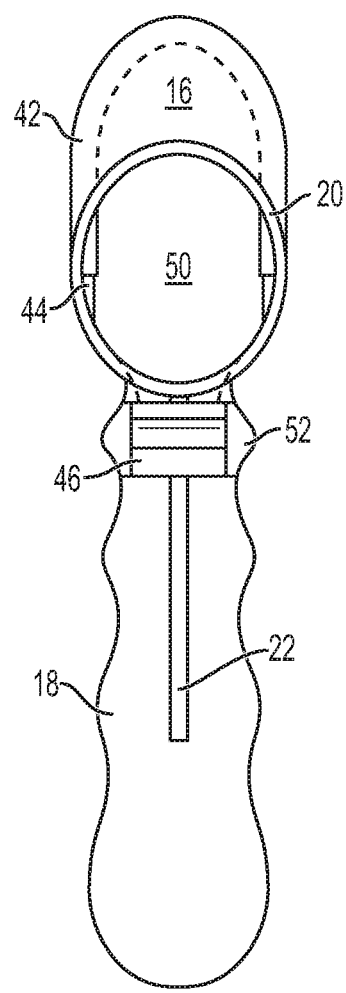
FIG. 3 depicts a back view of the exemplary dilation device of FIG. 1.

Tubular portion 20 may be positioned at a middle portion of the speculum 10, at a distal end of the handle 18, and about a proximal end of the lower jaw 24. Tubular portion 20 may include a planar proximal face 28, or a slightly curved proximal face as shown in FIG. 2. Distal face 30 of tubular portion 20 may include a curve or taper as shown in FIG. 2 such that a bottom portion 32 of the tubular portion 20 adjacent the lower jaw 24 may extend more distal than a top portion 34 of tubular portion 20. Tubular portion 20 may be circular in shape, or may be oval, such as oval from top to bottom as shown in FIG. 3. As best shown in FIG. 3, tubular portion 20 may include a lumen 50 extending completely therethrough. Finally, tubular portion 20 may include passageways 36 for portions of loop actuator 14, as will be described in more detail below.

Lower jaw 24 may extend distally from handle 18 and tubular portion 20 and form a distal end of body 12. Further, lower jaw 24 may extend generally parallel to tubular portion 20. Lower jaw 24 may be generally rectangular as shown, and may have a width approximately equal to the width of the tubular portion 20. Alternatively, lower jaw 24 may taper proximal toward a distal end 38 thereof, and/or may include a concavity as viewed from above the lower jaw 24. Lower jaw may include a straight distal end 38 as shown, or may include a curved distal-most end 38. Body 12, including handle 18, tubular portion 20, and lower jaw 24 may be formed as a one-piece integral unit using any conventional process. Body 12 maybe formed of any appropriate material, such as metal, polymer, or composite material.

As noted above, sheath 16 may extend from tubular portion 20 to loop actuator 14. Sheath 16 may include a generally rectangular panel of polymer material, such as silicone, and may be secured via glue or any conventional manner to an outer surface of tubular portion 20. In particular, sheath 16 may be secured at a proximal-most outer circumference 40 of tubular portion 20. Sheath 16 may extend less than the full outer circumference of the tubular portion 20. For example, sheath 16 may be omitted along a portion of the bottom of tubular portion 20 adjacent handle 18. The distal end of sheath 16 may include a tube 42 to receive loop actuator 14. The tube 42 may be a rolled portion of sheath 16, or could be a separate tube element rigidly secured to the distal end of sheath 16.

Loop actuator 14 may include a movable element, such as a push member 46 and a wire 44 extending in a loop such that both ends of the wire 44 are fixedly coupled to the push member 46. The push member 46 may be secured to handle 18 to allow for movement within actuator groove 22 to actuate opening and closing of speculum 10. Push member 46 may be have any shape or configuration and may include ridges or protrusion to assist in engagement by an operator. Passageways 26 in handle 18, passageways 36 in tubular portion 20 and/or passageways (not shown) in lower jaw 24 may provide a path for wire 44 toward a distal end of speculum 10. Wire 44 may exit body 12 at a mid portion thereof, adjacent a distal face 30 of tubular portion 20. Wire 44 of loop actuator 14 may extend through the tube 42 at the distal end of sheath 16 and loop back through body 12 to push member 46. Wire 44 may be a metal wire, or could be any similar rod, cord, tube, cable, etc. Further, wire 44 may be formed of sufficient rigidity to urge sheath into the open and closed configurations of FIGS. 1 and 2. Wire 44 may also have an at-rest loop shape. For example, wire 44 may be formed of a shape-memory material such as Nitinol preset into a loop shape. Additionally or alternatively, sheath 16 may include a preset curve shape as shown in FIG. 1.

The operation of speculum device will now be described. By moving the push member 46 of loop actuator 14 upward along the actuator groove 22, the speculum 10 can be changed from a closed position (FIG. 2) to an open position (FIG. 1). In this situation, the wire 44 can be moved first forward and then upward due to the tension created by the expanded sheath 16. The push member 46 can be locked in a locking recess 52 in order to maintain the speculum 10 in the open position. The shape of the opening at the distal end of the speculum 10 can conform to the shape of the internal wall of a body lumen, such as the vagina, rectum, mouth, or other naturally occurring orifices. When the speculum 10 is in its open position, any medical devices can be inserted through the lumen 50 of the tubular portion 20 for any medical procedures or treatments on the interior portion of or the tissue inside the body lumen, including medical camera and light devices. By moving the push member 46 downward along the actuator groove 22, the speculum 10 can be changed from the open position (FIG. 1) to the closed position (FIG. 2). In this situation, the wire 15 can be moved backward and downward. When in its closed position, the speculum 10 maintains a low profile for easy removal from the body lumen.

As shown in FIG. 1, sheath 16 forms a gap from lower jaw 24 when in the open configuration. In the closed configuration, sheath 16 closes the gap with lower jaw 24, and extends beyond distal end of lower jaw 24. Thus, in the closed configuration, the distal end of speculum 10 may include the flexibility of the loop actuator 14. Further, sheath 16 may include one or more reinforcing ribs of thicker material or separate material. Further, as discussed above wire 44 and/or tube 42 may provide the biasing force to urge sheath into the open configuration, additional biasing elements may be included (e.g., springs or biasing ribs). Finally, speculum 10 may include any appropriate coatings (e.g., hydrophilic or hydrophobic coatings) consistent with use in medical procedures.

Figure 4:
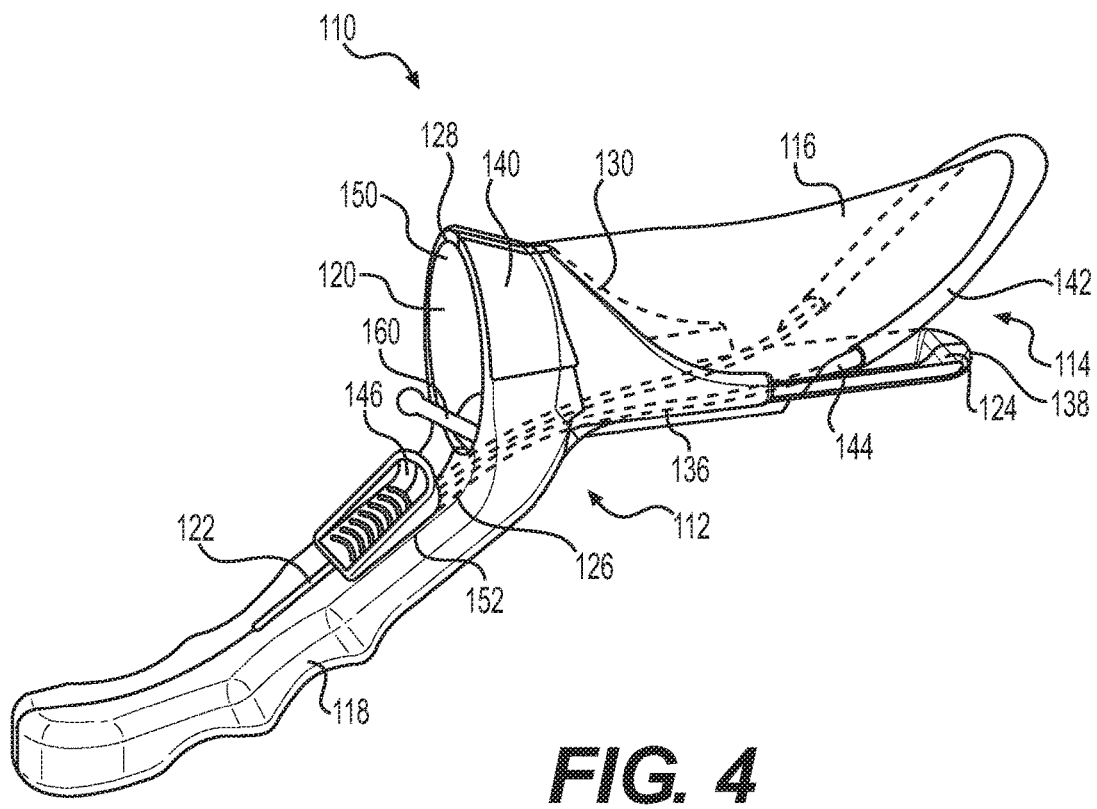
FIG. 4 depicts another exemplary dilation device in its open position.
Figure 5:
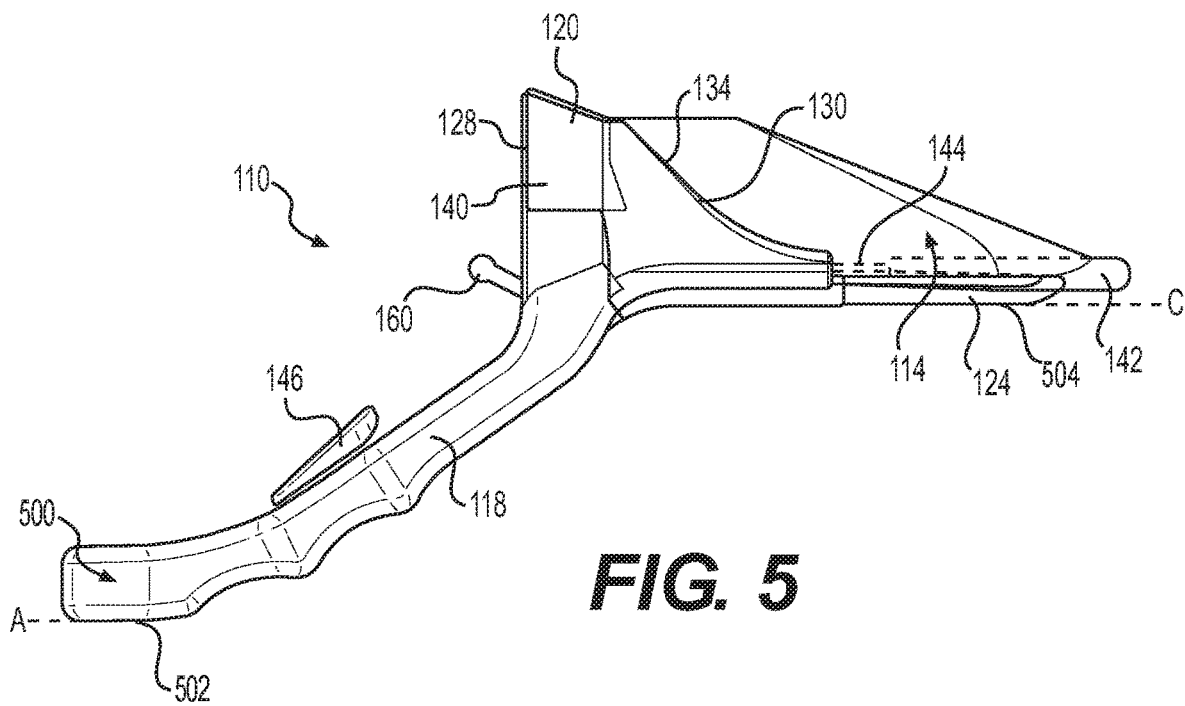
FIG. 5 depicts the exemplary dilation device of FIG. 4 in a closed position.

Another aspect of the present disclosure is depicted in FIGS. 4 and 5 as a dilation device, such as a speculum 110. FIG. 4 shows a perspective view of speculum 110 in an open configuration. FIG. 4 includes a body 112, a loop actuator 114 attached to the body 112, and a movable sheath 116 that is attached to the body 112 at a proximal end and to loop actuator 114 at a distal end. The body 112 may include a handle 118, a tubular portion 120 located at a distal end of the handle 118, and a lower jaw 124 including distal end 138 of lower jaw 124. The handle 118 extends proximally to provide a grip for the speculum 110. The handle 118 may be angled relative to the lower jaw 124 to form an obtuse angle to facilitate a comfortable and/or ergonomic use of the speculum 110 for patients or medical practitioners, or both. A proximal end portion 500 of handle 118 may include a substantially planar bottom surface 502, and bottom surface 502 may have a planar axis A (shown in FIG. 5) which extends through and/or aligns with the plane of bottom surface 502. The planar axis A of bottom surface 502 may be substantially parallel to a planar axis C of a bottom surface 504 of lower jaw 124. Planar axis C may extend through and/or align with a plane of bottom surface 504. Proximal portion 500 may prevent a user's hand from interfering with a table and/or bench that a patient may be resting on, which might hinder the range of motion of speculum 110. Handle 118 may be angled such that handle 118 extends proximally away from tubular portion 120, which may position a user's hand away from a patient's body during operation of speculum 110. The handle 118 may include an actuator groove 122 extending centrally along a proximal side of the handle 118. The actuator groove 122 is configured to guide movement of the loop actuator 114 between the speculum open and closed positions. Further, the actuator groove 122 may include a locking recess 152 for securing the loop actuator 114 in the open configuration. The handle 118 may also include internal passageways 126 for distally extending portions of the loop actuator 114. The handle 118 may be in any shape, size, or design. For instance, the handle may be in the shape of cylinder, cone, cuboid, or triangular prism, and may include any conventional gripping grooves such as the grooves shown.

Tubular portion 120 may be positioned at a middle portion of the speculum 110, at a distal end of the handle 118, and about a proximal end of the lower jaw 124. Tubular portion 20 may include a planar proximal face 128, distal face 130, a lumen 150, passageways 136, and outer circumference 140.

Sheath 116 may include a tube 142 at a distal end of sheath 116 to receive loop actuator 114. Loop actuator 114 may include a movable element, such as a push member 146, and a wire 144 extending in a loop such that both ends of the wire 144 are fixedly coupled to the push member 146. The push member 146 may be secured to handle 118 to allow for movement within actuator groove 122 to actuate opening and closing of speculum 110. Passageways 126 in handle 118, passageways 136 in tubular portion 120 and/or passageways (not shown) in lower jaw 124 may provide a path for wire 144 toward a distal end of speculum 110. In some examples, sheath 116 may be flexible, may expand from a retracted position to an expanded position, and may be biased towards the retracted position. Any of the components of speculum 110 may have any of the features described in connection with the components of speculum 10.

Figure 6:
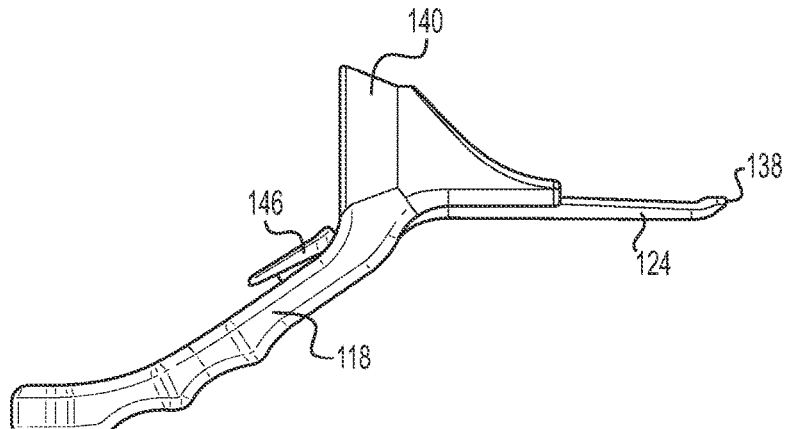
FIG. 6 depicts a portion of the exemplary dilation device of FIG. 4.
Figure 7:
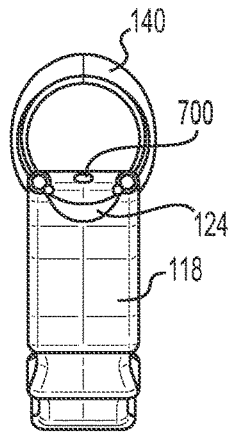
FIG. 7 depicts a front view of the portion of the exemplary dilation device shown in FIG. 6.

Speculum 110 may include an integrated light source 700 (shown in FIGS. 7 and 8) positioned within or partially within handle 118, tubular member 120, and/or lower jaw 124. Integrated light source 700 may include one or more light emitting diodes (LEDs), one or more fiber optic light sources, or any other light source known in the art. Integrated light source 700 may be configured to direct light in a distal direction, and may be configured to illuminate an internal wall of a body lumen, such as the vagina, rectum, mouth, or other naturally occurring orifices. FIGS. 6 and 7 show side and front views of handle 118, push member 146, lower jaw 124 including distal end 138, and outer circumference 140 of tubular member 120. Loop actuator 114 and sheath 116 are removed in FIGS. 6 and 7. As shown in FIG. 7, light source 700 may be positioned at a distal portion of handle 118, a proximal portion of lower jaw 124, and/or a lower portion of tubular member 120 proximate to handle 118 and/or lower jaw 124. Light source 700 may be aligned with a central longitudinal axis of speculum 110 and may be positioned distal to the proximal end of tubular member 120. In some examples, light source 700 may be entirely within the speculum 110 and not exposed, and in other examples light source is partially exposed. In some examples, a portion of any one or more handle 118, a proximal portion of lower jaw 124, tubular member 120, and lower jaw 124 may include a transparent window covering light source 700. A recess 139 may extend longitudinally from a proximal portion of lower jaw 124 to a distal portion of lower jaw, and recess 139 may face sheath 116. Recess 139 may provide additional space between lower jaw 124 and sheath 116, may guide tools moving through tubular member 120 adjacent to lower jaw 124, and may provide a lip 141 at a distal portion of lower jaw 124.

A pull tab 160 may be incorporated into speculum 110 and pull tab 160 may be configured to turn on and off light source 700. Pull tab 160 may be initially positioned within a portion of speculum 110, and a user may remove pull tab 160 by pulling pull tab 160 out of the speculum 110. Once pull tab 160 is removed from speculum 110, a circuit within speculum 110 may be completed which may cause light source 160 to receive electrical current from a battery 850 (shown in FIG. 8) or other source of electrical energy, and light source 700 may then illuminate. In some examples, removal of pull tab 160 from speculum 110 may cause two coin cell batteries to contact each other and drive voltage to operate light source 700. For example, pull tab 160 may be "sandwiched" between coin cell batteries (or any other type of battery known in the art, shown as battery 850 in FIG. 8) separating the positive terminal of one of the coin cell batteries from the negative terminal of another coin cell battery, and when the pull tab 160 is removed from the position between the two batteries, contact is made between the positive and negative terminals to actuate the LED (thus illuminate the light source 700). In some examples, battery 850 may be configured to provide enough energy to illuminate light source 700 for 30 minutes or longer. Alternatively, any other actuator (such as an integrated button on handle 118, switch, sensor, or other actuator known in the art) may be used to active light source 700.

Figure 8:
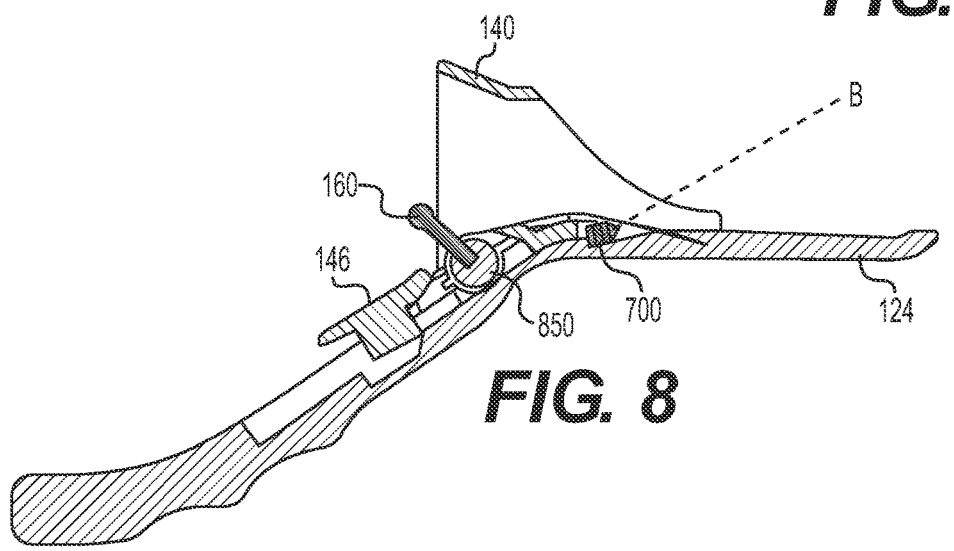
FIG. 8 depicts a side cross-sectional view of the portion of the exemplary dilation device shown in FIG. 6.

FIG. 8 shows a side, cross-sectional view of the portion of speculum 110 shown in FIGS. 6 and 7. As shown in FIG. 8, pull tab 160 may be positioned between battery 850 and light source 700. Internal wiring and/or other electrical connectors (not shown) may be positioned within speculum 110 to couple battery 850 to light source 700. As discussed hereinabove, light source 700 may be angled upward towards a central longitudinal axis of lumen 150. A central illumination axis B of light source 700 may extend upward from lower jaw 124 and may form an acute angle with lower jaw 124 (as shown in FIG. 8.) In some examples (shown in FIG. 8), light source 700 may be entirely distal of tubular member 120, and in other examples may be positioned entirely within tubular member 120 (not shown). By incorporating an integrated light source 700 into speculum 110, the illuminated field of view of the patient's anatomy may increase relative to conventional methods of illumination, and the user may avoid holding an additional medical device (such as a separate light source) during a procedure. Thus, incorporating light source 700 into speculum 110 may allow users to increase procedure efficiency and decrease procedure time.

Figure 9A:
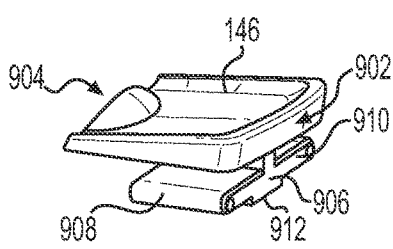
FIGS. 9A and 9B depict perspective and front views, respectively, of a component of the exemplary dilation device shown in FIG. 4.
Figure 9B:
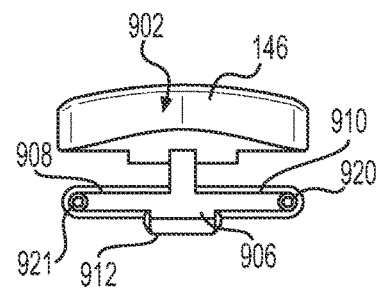

FIGS. 9A and 9B shown perspective and front views of push member 146. Push member 146 may include a distal end 902, proximal end 904, and a T-shaped protrusion 906. T-shaped protrusion 906 may include lateral extensions 908, 910 and a central portion 912 that extends downward. Guide lumens 920, 921 may be positioned at a lateral end of each lateral extension 908, 910. Guide lumens 920, 921 may be configured to receive and fixedly couple to ends of wire 144. T-shaped protrusion 906 may be sized to slide through actuator groove 122 and fit within locking recess 152. Locking recess 152 may be a recessed portion of actuator groove, as shown in FIG. 8, configured to received T-shaped protrusion and prevent proximal movement of T-shaped protrusion 906 when T-shaped protrusion 906 is positioned within locking recess 152.

The operation of speculum device 110 is substantially similar to the operation of speculum device 10, and any of the attributes described hereinabove in relation to speculum device 10 may apply to speculum device 110. By moving the push member 146 of loop actuator 14 upward along the actuator groove 122, the speculum 110 can be changed from a closed position (FIG. 5) to an open position (FIG. 4). In this situation, the wire 144 can be moved first forward and then upward due to the tension created by the expanded sheath 116. The push member 146 can be locked in a locking recess 152 in order to maintain the speculum 110 in the open position. Speculum device 110 may create an audible "click" sound when push member 146 is positioned within locking recess 152. Tension from sheath 116 applied to wire 144 may apply a force in the proximal direction on push member 146, which may maintain the position of push member 146 within locking recess 152. By the user first 1) moving push member 146 upward to move push member 146 out of locking recess 152, and then 2) moving the push member 146 downward along the actuator groove 122, the speculum 110 can be changed from the open position (FIG. 4) to the closed position (FIG. 5). In this situation, the wire 115 can be moved backward and downward. When in its closed position, the speculum 110 maintains a low profile for easy removal from the body lumen. Integrated light source 700 may be turn on (illuminated) by a user removing pull tab 160 at any time before, during, or after a procedure.

While principles of the present disclosure are described herein with reference to illustrative aspects for particular applications, it should be understood that the disclosure is not limited thereto. For example, while the device disclosed herein is discussed as a speculum dilation device 10, any type of dilation device is contemplated, or any such analogous device. Those having ordinary skill in the art and access to the teachings provided herein will recognize additional modifications, applications, aspects, and substitution of equivalents all fall within the scope of the aspects described herein. Accordingly, the present disclosure is not to be considered as limited by the foregoing description.

We claim:

1. A dilation device, the device comprising:
   a body including a tubular portion, a lower jaw extending distally from the tubular portion, and a handle portion extending proximally from tubular portion;
   a loop actuator attached to the body; and
   a sheath comprising a proximal end and a distal end, wherein the proximal end is attached to the tubular portion and the distal end is attached to the loop actuator;
   wherein a distal portion of the loop actuator is configured to transition from (i) a closed state in which the distal portion of the loop actuator longitudinally extends substantially parallel to the lower jaw to (ii) an open state in which the distal portion of the loop actuator longitudinally extends substantially transverse to the lower jaw.

2. The device of claim 1, wherein the loop actuator extends through a portion of the lower jaw and a portion of the handle portion.

3. The device of claim 2, wherein the loop actuator includes a wire having both ends coupled to a movable element located at the handle portion.

4. The device of claim 3, wherein the sheath extends circumferentially about a portion of the tubular portion.

5. The device of claim 4, wherein the distal end of the sheath includes a tube for receiving the wire of the loop actuator.

6. The device of claim 1, wherein the loop actuator extends distally from a distalmost end of the lower jaw in the closed state.

7. The device of claim 6, further comprising a push member coupled to a proximal end of the loop actuator, wherein the push member is configured to slide across the handle portion to transition the loop actuator from the closed state to the open state.

8. A dilation method for a dilation device including a body, a loop actuator attached to the body, and a sheath attached to the body and the loop actuator, wherein the body includes a tubular portion, a first jaw extending distally from the tubular portion, and a handle extending proximally from the tubular portion, the method comprising;
   placing the dilation device into a body lumen; and
   expanding the sheath from a retracted position to an expanded position by extending or retracting the loop actuator, wherein a distal portion of the loop actuator and a distal portion of the sheath moves upward relative to the first jaw as the sheath transitions from the retracted position to the expanded position.

9. The method of claim 8, further comprising performing a treatment on an interior portion of the body lumen through the tubular portion of the body of the dilation device.

10. The method of claim 8, further comprising activating an integrated light source on the dilation device.

11. A dilation device, the device comprising:
    a body including a tubular portion, a lower jaw extending distally from the tubular portion, and a handle portion extending proximally from tubular portion;
    a loop actuator attached to the body;
    a sheath comprising a proximal end and a distal end, wherein the proximal end is attached to the tubular portion and the distal end is attached to the loop actuator; and
    a light source positioned within the body;
    wherein the lower jaw is substantially planar; and wherein a distalmost portion of the loop actuator is configured to transition from (i) a closed position in which the distal portion of the loop actuator is substantially parallel to the lower jaw, and (ii) an open position in which the distal portion of the loop actuator curves away from the lower jaw.

12. The device of claim 11, wherein the body includes a pull tab configured to actuate illumination of the light source.

13. The device of claim 11, wherein the light source includes a central illumination axis extending away from the lower jaw.

14. The device of claim 11, wherein the light source is positioned distal to the handle portion of the body.

15. The device of claim 11, further comprising a battery positioned within the body.

16. The device of claim 11, wherein the light source is positioned within the tubular portion.

17. The device of claim 16, further comprising a pull tab configured to actuate illumination of the light source, wherein the pull tab is positioned within the tubular portion.

18. The device of claim 11, further comprising a push member, wherein the push member is fixedly coupled to the loop actuator, and wherein the body includes a groove configured to receive the push member.

19. The device of claim 18, wherein the push member includes a T-shaped extension positioned within the groove.

20. The device of claim 18, wherein opposing ends of the loop actuator are coupled to the push member.

* * * * *